United States Patent [19]

Kuhlman

[11] Patent Number: 4,875,235
[45] Date of Patent: Oct. 24, 1989

[54] WELDER'S MASK WITH BREATH CONTROLLED EYE SHIELD

[76] Inventor: Thomas E. Kuhlman, R.R. 7748, Spirit Lake, Iowa 51360

[21] Appl. No.: 224,667

[22] Filed: Jul. 27, 1988

[51] Int. Cl.⁴ .............................................. A61F 9/06
[52] U.S. Cl. ........................................... 2/8; 219/147; 200/83 J
[58] Field of Search ................ 2/8; 200/83 J; 219/147

[56] References Cited

U.S. PATENT DOCUMENTS

| | | | |
|---|---|---|---|
| 3,260,816 | 7/1966 | Schad | 200/83 J |
| 3,833,936 | 9/1974 | Lo Guidice | 2/8 |
| 3,890,646 | 6/1975 | Fassett et al. | 2/8 |

Primary Examiner—Peter Nerbun
Attorney, Agent, or Firm—Zarley, McKee, Thomte, Voorhees & Sease

[57] ABSTRACT

A welder's mask with breath-activated eye shield which includes a conventional welder's mask housing with hardware for mounting upon a welder's head. A viewing opening exists in the mask housing which receives a welder's eye shield into an eye shield framework. A power source and motor are mounted to the mask housing. A linkage is attached between the shaft of the motor and the eye shield. The motor operates to turn the shaft in either rotational direction causing the linkage to move the eye shield out of the eye shield framework or into the eye shield framework according to the welder's choice. Operation of the motor is controlled by a breath-activated switch. An air chamber includes an aperture covered by a resilient diaphragm. A tube is connected to a second aperture in the air chamber. The welder exhales to outwardly flex the diaphragm from the chamber and inhales to inwardly flex the diaphragm. A rigid stem is connected between the diaphragm and an electrically conductive element. The electrically conductive element can thus be moved between two positions depending on whether the welder inhales or exhales. Two different signals can thus be sent to the motor to operate it in opposite directions according to choice.

19 Claims, 1 Drawing Sheet

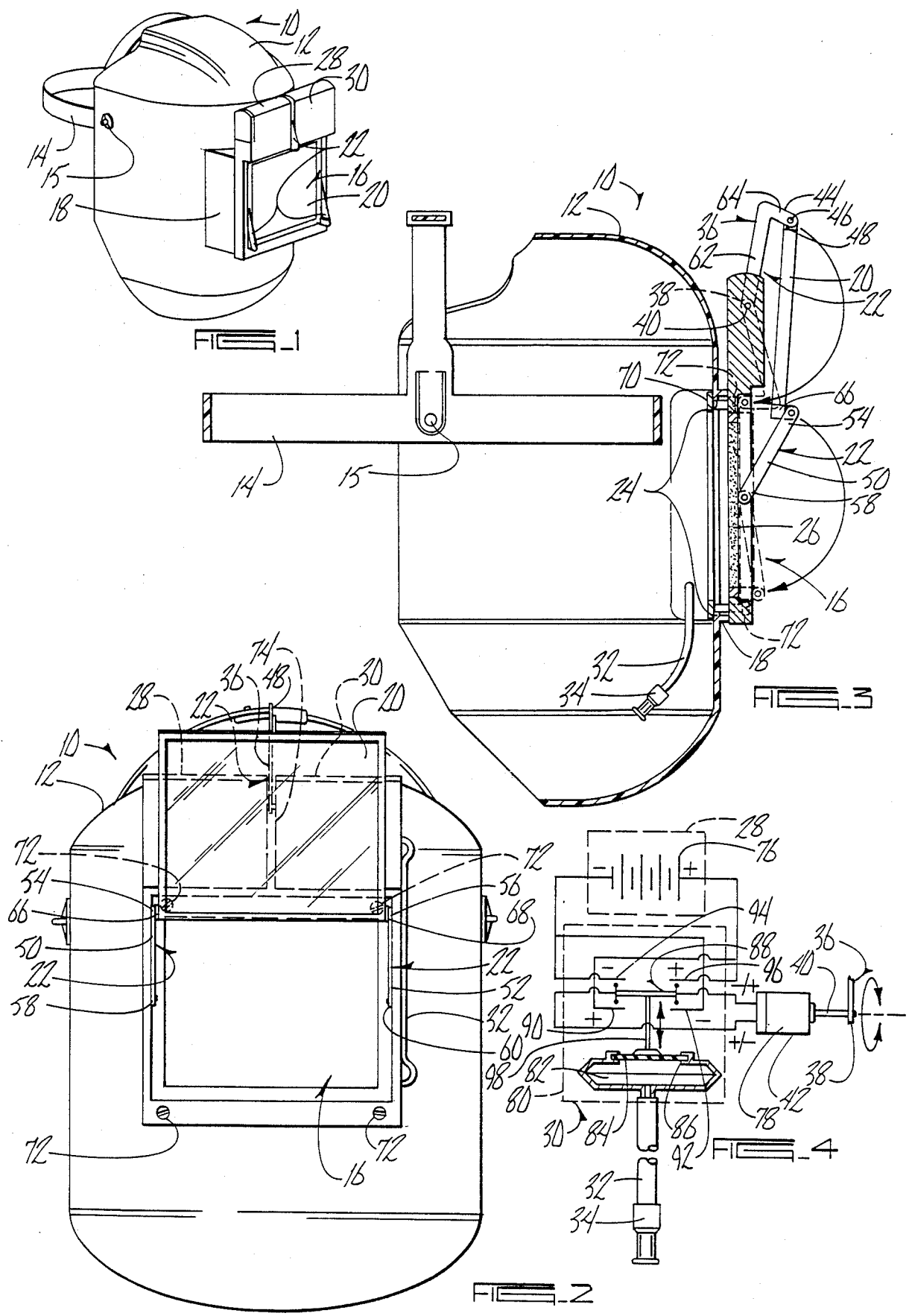

WELDER'S MASK WITH BREATH CONTROLLED EYE SHIELD

BACKGROUND OF THE INVENTION a. Field of the Invention

This invention relates to welding masks and in particular, to welding masks having openable eye shields.

b. Problems in the Art

Welding masks are required to protect the face and eyes of the welder. Not only does it protect against the heat, sparks, and debris from hitting the welder's face and head, an eye shield also filters out harmful light, or reduces intensity of the light produced in different types of welding in order to protect the welders eyes.

Conventionally, welder's masks cover the top, sides, front, and neck area of the welder, and are removably positionable on the welder's head by adjustable straps or a cage. Because the eye shield is required to be made of very dark glass, it is difficult to see out of the mask and eye shield when not welding.

Therefore, traditional welding masks are pivotable upon the head strap or cage to allow the welder to flip the mask up when needed. This, of course, is time consuming and somewhat cumbersome, because the welder must use one free hand to do so. Repeated pivoting of the welding mask is tiresome.

There have been some attempt to improve upon this problem. Some welder's masks have independently pivotal eye shields. While it is less difficult to pivot the eye shield, rather than the entire mask, it still requires the manual effort and the freedom of one hand to do so. There have been some attempts to utilize a mechanically operated eye shield. Generally these require the welder to push a button or turn a switch which in turn mechanically pivots the eye shield open or closed. This again requires a free hand of the welder to operate the switch. It also requires some power source. If the power source is AC electrical power, the helmet must have a cord plugged into an electrical outlet, which limits movement of the welder. If battery powered, it still requires electrical circuitry to the motor, and to the switch.

Other attempts have tried to eliminate the need for the welder to use one free hand to reach up to the mask to push a switch, or manually open the eye shield. They utilize switches which are connected by wires toward the work area of the welder so that the welder does not have to reach up to the helmet. Others wire the switch to a production line wherein the switch is tripped by the passing of work objects on the line. Again, this requires the wiring to be directly connected to the helmet which limits movement of the welder and can be dangerous, or at least it can get in the way of welding operations.

The present inventor previously improved upon control of the eye shield of the welder's mask by inventing a remote controlled eye shield. As disclosed in U.S. Pat. No. 4,679,255, the controller for actuating opening and closing of the eye shield of a welder's mask was actuated by using a radio transmitter. Therefore, all cords and wires to the welder's mask were eliminated. The transmitter could then be set in any convenient location, including being automatically tripped by work pieces along a production line, or other automatic actuations. The welder's mask was then required to carry linkage and a motor to open and close the eye shield, and a radio receiver and power source. All these could be incorporated on or within the welder's mask with minimal weight and intrusion.

The inventor has discovered that there is still room for improvement over the state of the art, especially in welding situations where it is inconvenient to utilize hands or feet to actuate a control, even if it is conveniently placed. There is further room for improvements in situations where automatic actuations of the switch controlling the eye shield is not possible, or where the welder needs to move to various positions where it is not convenient to carry a switch along.

It is further desirable to improve upon the economics, reliability, and compactness of the structure for allowing mechanical control of the eye shield. It would also be advantageous to be able to retrofit existing welding helmets with such mechanical control.

It is therefore the principle object of the present invention to provide a welder's mask with a breath controlled eye shield which solves or improves over the problems and deficiencies in the art. Another object of the present invention is to provide a welder's mask as above described which completely eliminates the need for use of the welder's hands or feet to control operation of the eye shield.

Another object of the present invention is to provide a welder's mask as above described which relies completely on the welder's inhaling and exhaling to control the opening and closing of the eye shield.

A further object of the present invention is to provide a welder's mask as above described which can be totally self-contained in a compact self-powered unit mounted unobtrusively on or in the welder's mask.

Another object of the present invention is to provide a welder's mask as above described which can effectively and reliably open and close the eye shield of a welder's mask, and keep it tightly sealed when in a closed position.

Another object of the present invention is to provide a welder's mask as above described which is economical, efficient, and durable.

Another object of the present invention is to provide a welder's mask as above described which can be easily incorporated into newly manufactured welder's masks or retrofitted onto existing masks.

Further objects, features, and advantages of the invention will become more apparent with reference to the accompanying specification and claims.

SUMMARY OF THE INVENTION

The present invention relates to a welder's mask having a breath activated eye shield. A conventional welder's helmet includes a mask housing having a viewing opening, along with a means for mounting the mask to a welder's head. An eye shield is moveably associated with the mask housing so that it can be moved between a position sealing and covering the viewing opening, to a position that moves away from the viewing opening to allow the welder to have unobstructed vision out the viewing opening.

A linkage extends from the eye shield to a motor means which can move the eye shield from a closed position to an open position and back to a closed position. A battery means is also associated with the motor to power it.

Operation of the motor is controlled by a special switching means which instructs the motor to either open or close the eye shield. The switching means in turn is controlled by the inhaling and exhaling of the welder through a tube held in the welder's mouth which is connected to the switching means. Inhaling to a certain suction level causes the eye shield to move in one direction, whereas exhaling to a certain pressure level causes the eye shield to move in opposite direction.

The welder therefore is allowed complete control of the eye shield without any use of hands, feet, or other actuation except for a certain magnitude of inhaling and exhaling. The control means for the eye shield is entirely integrated with the helmet, is unobtrusive, light weight, and totally portable.

BRIEF DESCRIPTION OF THE DRAWINGS

FIG. 1 is a perspective view of the invention.

FIG. 2 is a elevational view of the invention.

FIG. 3 is a side cross-sectional elevational view of the invention.

FIG. 4 is a schematic of the operational circuitry of the invention.

DETAILED DESCRIPTION OF THE PREFERRED EMBODIMENT

With reference to the drawings, a preferred embodiment of the invention will now be described. It is to be understood that the preferred embodiment is given by way of example only and not by way of limitation. Like parts will be referred to by like reference numerals in all of the drawings.

With particular reference to FIG. 1, a welder's mask 10, according to the present invention is shown in perspective. A mask housing 12 made out of metal, rigid plastic, or other durable and heat resistant material is configured so as to cover the front, and a majority of the top, sides, chin and front neck of a welder's head when in position. Housing 12 is retained on a welder's head by mounting straps 14, which are adjustable for various sized heads. Mounting straps 14 form a cage to hold the mask on the welder's head. The mask is pivotable about pivots 15 on either side of the users head to allow the whole mask housing 12 to be tilted upwardly when desired.

Mask housing 12 also contains a viewing opening 16 which is configured to provide line of sight for the welder when mask 10 is positioned on the welder's head. In the preferred embodiment, viewing opening 16 is framed by an eye shield framework 18 which presents a planar frame to a planar eye shield 20 which is made out of conventional darkly colored protective glass or plastic, such as is conventional in welder's masks.

As can be seen in FIG. 1, eye shield 20 is movable out of eye shield framework 18 to give unobstructed vision of the welder through viewing opening 16. Linkage members 22 provide this adjustability. The interior of eye shield framework 18 has ridges 24 which with gasket 26 provide a seal for eye shield 20 when brought to a closed position within eye shield framework 18. Above eye shield framework 18 there exist a battery compartment 28, and a servo motor and switch compartment 30. A hose 32 is directly connected to the servo motor and switch compartment 30, and the end of hose 32 contains a replaceable mouth piece 34.

FIG. 2 depicts the positioning and relationship of various linkage members 22 with the battery and servo motor/switch compartments 28 and 30. An upper linkage member 36 is rigidly connected at end 38 to motor shaft 40. Motor shaft 40 is directly connected to a small DC servomotor 42 (not shown), such as are well know within the art. Servo motor 42 upon instruction, can rotate shaft 40 in either direction. End 44 of upper linkage member 36 is pivotally attached by a pivot pin 46 to tab 48 which is rigidly secured to the top edged of eye shield 20.

Side linkage members 50 and 52 are pivotally attached at ends 54 and 56 respectively to opposite lower side ends of eye shield 20, and are pivotally attached at ends 58 and 60 to opposite middle sides of eye shield framework 18.

It is therefore to be understood that any rotation of motor shaft 40 would cause movement of upper linkage member 36. Upper linkage 36, being pivotally attached to tab 48 of eye shield 20 would cause movement of eye shield 20. Side linkage members 50 and 52 would insure that any movement of eye shield 20 is stable and accurate so that eye shield 20 can be repeatable moved out of eye shield framework 18 and back into sealing relationship into eye shield framework 18.

Therefore, this relationship allows eye shield 20 to be sealing secured in eye shield framework 18 so that no gaps exist for hazardous welding arc light to pass into the welder's eyes, and no particles, debris or gases would easily pass the sides of eye shield 20.

FIG. 3 shows in more detail, the possible movement of eye shield 20 between a closed and an open position. When eye shield 20 is in an open position, it is raised outwardly and upwardly from eye shield framework 18. This is shown by the solid lines in FIG. 3. It can be seen that upper linkage member 36 is basically in the shape of the numeral "7" having a long portion 62 attached to a motor shaft 40 at end 38, and short portion 64 attached at end 44 pivotally (by point pin 46) to tab 48 of eye shield 20. Short portion 64 forms an acute angle with long portion 62 with respect to that side of the upper linkage member 36 which faces eye shield 20. This configuration for upper linkage member 36 allows eye shield 20 to be first moved away from eye shield frame 18 and then moved upwardly away from viewing opening 16 upon rotation of upper linkage member 36 between the closed position and the open position for eye shield 20. This advantageously allows eye shield 20 to be moved as far as possible out of the viewing range for the welder utilizing welder mask 10.

FIG. 3 also shows that side linkage members 50 and 52 are pivotal by means which are known within the art along the side of eye shield framework 18. Their outer ends are pivotal to tabs 66 and 68 on the outer and lowers ends of eye shield 20.

FIG. 3 also depicts that compartment 28 and 30 for the battery, servomotor, and switch components can be fairly thin and integrated with the eye shield framework 18. By appropriate mounting structure, such as receiver plate 70, the entire assembly including compartments 28 and 30, eye shield framework 18, linkage members 22, and eye shield 20, can be clamped as a unit to mask housing 12, through viewing opening 16. FIG. 3 shows that this can be accomplished by screws 72 which would secure, and bring together in a clamping manner, receiver plate 70 and eye shield framework 18. This allows the invention to easily installed, removed, replaced, and serviced. It also allows the invention to be retrofitted to existing welding masks.

By referring to FIGS. 1–3 it is also pointed out that a slot 74 exists between battery compartment 28 and servo motor and switch compartment 30. Slot 74 allows upper linkage member 36 to be recessed so that it is roughly directly vertically above and in a plane defined by eye shield framework 18. The side linkage members 50 and 52, on the other hand, are foldable, at least partly, into gaps around the vertical sides of eye shield framework 18.

FIG. 4 depicts schematically the circuitry utilized in operating the invention. A battery 76 is utilized to power the electrical circuitry and components. The direct current servo motor 78 is controlled by the breath activated switch 80. As can be seen, hose 32 is directly connected to a chamber 82. A rubber diaphragm 84 is stretched across an aperture 86 to chamber 82, and held in position there.

A conductive element 88 is movable positioned between first and second sets of contacts 90, 92, and 94, 96. A stem 98 is attached between diaphragm 84, and conductive element 88. As can be seen in FIG. 4, the first set of contacts 90 and 92 are connected respectively to the positive and negative sides of battery 76. Conversely, the second set of contacts 94 and 96 are connected to the negative and positive sides respectively of battery 76. The inputs to servo motor 78 are connected to the opposite ends of conductive element 88.

Breath activated switch 80 is constructed so that conductive element 88 is normally held biased and in a position intermediate between the first set of contacts 90, 92, and the second set of contacts 94, 96. In that position, a basically open circuit exists between battery 76 and motor 78. Therefore, eye shield 20 remains in position. However, when the welder exhales or inhales to a sufficient level, rubber diaphragm 84 will either be depressed or bulge outwardly which will in turn cause conductive element 88 to contact the first or second set of contacts. An electrical pathway will therefore be formed to motor 78, causing it to operate for as long as conductive element 88 is held in that conducting position.

It can therefore be understood that, as is well known within the art, servo motor 78 would turn in one direction when conductive element 88 is activated and abuts contacts 90, 92 and will rotate in an opposite direction when the second set of contacts 94 and 96 are bridged by conductive element 88. The welder thus has control of both directions of rotations of motor 78 depending on whether the welder inhales or exhales.

It is to be further understood that this allows the welder to have complete control of the amount of opening or closing of eye shield 20. In other words, if the welder inhales and begins moving eye shield 20, any stopping of inhaling will also stop movement of eye shield 20, even if it is part way open or closed. Thus, if the welder wants to open the eye shield 20 only a slight ways and for a short period, he can open eye shield 20 only a small ways and then quickly closing again by quickly reversing his/her breathing. Partial closing can similarly be achieved.

It will be appreciated that the present invention can take many forms and embodiments. The true essence and spirit of this invention are defined in the appended claims, and it is not intended that the embodiment of the invention presented herein should limit the scope thereof.

What is claimed is:

1. A welder's mask having a breath controlled eye shield which is efficient in size, weight, and operation comprising:
    a mask housing having a viewing opening and means for mounting the mask housing upon the head of a user;
    a modular, self-contained breath controlled eye shield means, having mounting means for adaptable and removable positioning on the mask housing and viewing opening, and including;
    a welder's eye shield being movable between a closed position sealing and covering the viewing opening and an open position uncovering the viewing opening in the mask housing;
    a motor means having a drive-shaft and being mounted in the eye shield means and operatively connectable to a power source mounted in the eye shield means, the motor means having connective linkage means attached between the eye shield and the motor means, drive-shaft of the motor means being operable in the first and second rotational directions to move the connective linkage means to correspondingly move the eye shield to any resting position between and including the open and closed positions;
    a switch means operatively connected to the motor means for controlling operation of the motor means int he first and second rotational directions for the drive-shaft, said switch means comprising:
    enclosed chamber means including first and second apertures;
    a hose connected in fluid communication to the first aperture;
    a resilient diaphragm sealing and covering the second aperture;
    an electrically conductive element, external of the enclosed chamber means, movable between first and second conducting positions;
    a stem, external of the enclosed chamber means, connected between the electrically conductive element and the diaphragm;
    so that when exhaled air from the user is introduced into the hose, the pressure inside the air chamber increases and flexes the diaphragm outwardly causing the stem to push the electrically conductive element towards the first conducting position, and inhaling causes a reduction in air pressure in the air chamber int urn causing inward flexing of the diaphragm, the stem pulling the electrically conductive element towards the second conducting position, the change of the conductive element between the first and second conducting positions electrically switching the operation of the motor means between the first and second rotational directions.

2. The welder's mask of claim 1 wherein the power source comprises a battery means.

3. The welder's mask of claim 1 wherein the power source comprises an electrical conduit means connectable to electrical power.

4. The welder's mask of claim 1 wherein the connective linkage means is rigidly fixed generally transversely to a rotational axis of the drive shaft of the motor means.

5. The welder's mask of claim 1 wherein the connective linkage means includes a first arm having a first end attached to the drive shaft of the motor means and a second end pivotally attached to the eye shield.

6. The welder's mask of claim 5 wherein the first arm comprises a first portion extending from the drive shaft, and a second portion extending to the eye shield.

7. The welder's mask of claim 6 wherein the first portion of the first arm is angularly related to the second portion.

8. The welder's mask of claim 7 wherein the angular relation of the first and second portions of the first arm is an oblique angle.

9. The welder's mask of claim 5 wherein the connective linkage means further comprises at least one additional arm hingeably connected at opposite ends between the masked housing and the eye shield.

10. The welder's mask of claim 9 wherein the first arm of the connective linkage means is attached generally to the upper portion of the eye shield, and any additional arm is attached generally to the bottom of the eye shield.

11. The welder's mask of claim 1 wherein inhaling and exhaling through a conduit means comprises breath control of the switch means.

12. The welder's mask of claim 1 wherein the switch means has at least two switching positions.

13. The welder's mask of claim 12 wherein at least one switching position is related to whether a sufficient level of breath control is providing through the conduit means.

14. The welder's mask of claim 13 wherein a biasing means normally retains said diaphragm in an inoperative position.

15. The welder's mask of claim 14 wherein said flexing of said diaphragm occurs by overcoming the force of the biasing means holding the switching means in an inoperative position.

16. The welder's mask of claim 13 wherein at least two positions are related to whether a sufficient level of breath control is providing through the conduit means.

17. The welder's mask of claim 1 wherein inhaling and exhaling respectively controls operation of the motor means in the first and second rotational directions.

18. The welder's mask of claim 17 wherein the switch means includes a biasing means for disallowing operation of the motor means in the first and second rotational directions unless the force of the biasing means is sufficiently overcome by activation of the switching means by inhaling or exhaling by the user.

19. The switching means of claim 1 wherein the switching means is connectible to a motor means and movement of the conductive element to the first conducting position causes a shaft of the motor means to rotate in a first rotational direction, and movement of the connective element to the second conducting position causes rotation of the shaft of the motor means in a second rotational direction.

* * * * *